United States Patent [19]

Yamamoto et al.

[11] Patent Number: 5,290,246

[45] Date of Patent: Mar. 1, 1994

[54] PIERCING NEEDLE

[75] Inventors: Masanobu Yamamoto; Kouhei Hayashi, both of Fujinomiya, Japan

[73] Assignee: Terumo Kabushiki Kaisha, Tokyo, Japan

[21] Appl. No.: 960,538

[22] Filed: Oct. 13, 1992

Related U.S. Application Data

[63] Continuation-in-part of Ser. No. 821,426, Jan. 15, 1992, Pat. No. 5,242,411.

Foreign Application Priority Data

Jan. 18, 1991 [JP] Japan ............... 3-001181[U]
Oct. 15, 1991 [JP] Japan ............... 3-092600[U]

[51] Int. Cl.[5] .................................................. A61M 5/178
[52] U.S. Cl. ........................................................... 604/167
[58] Field of Search ............... 604/168, 126, 264, 164, 604/167, 93

References Cited

U.S. PATENT DOCUMENTS

| 4,149,535 | 4/1979 | Volder | 128/214.4 |
| 4,200,096 | 4/1980 | Charvin | 604/168 X |
| 4,610,665 | 9/1986 | Matsumoto et al. | 604/167 |
| 4,675,017 | 6/1987 | Sato | 604/126 X |
| 4,682,980 | 7/1987 | Suzuki | 604/168 X |
| 4,917,671 | 4/1990 | Chang | 604/168 |
| 4,935,010 | 6/1990 | Cox et al. | 604/122 |
| 5,032,116 | 7/1991 | Peterson et al. | 604/168 |
| 5,104,389 | 4/1992 | Deem et al. | 604/167 X |

FOREIGN PATENT DOCUMENTS

| 0139091 | 5/1985 | European Pat. Off. |
| 0223451 | 7/1987 | European Pat. Off. |
| 0268480 | 5/1988 | European Pat. Off. |
| 60-88562 | 5/1985 | Japan |
| 63-197463 | 8/1988 | Japan |

Primary Examiner—Gene Mancene
Assistant Examiner—Jeffrey A. Smith
Attorney, Agent, or Firm—Frishauf, Holtz, Goodman & Woodward

[57] ABSTRACT

A piercing needle with which a flashback can be reliably confirmed and air can be prevented from remaining in its hub portion. The piercing needle comprises an outer needle having a hub, an inner needle to be inserted into the outer needle, a hub portion of which is adapted to be fitted in the outer needle hub, and a valve disc to close the internal cavity of the outer needle. Side holes are formed in the distal end of the outer needle. The outer needle hub is made in two parts, and is provided with a hydrophobic vent filter near the valve disc to allow the internal cavity of the outer needle hub to communicate with the outer atmosphere.

5 Claims, 9 Drawing Sheets

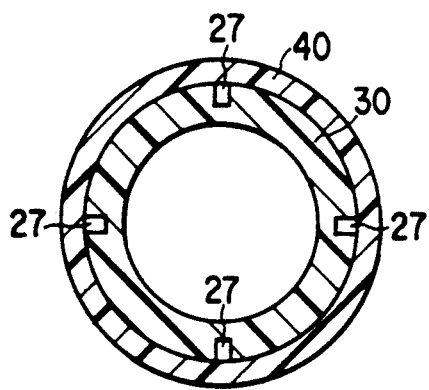
F I G. 4
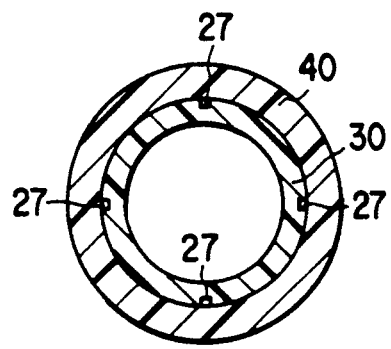
F I G. 5
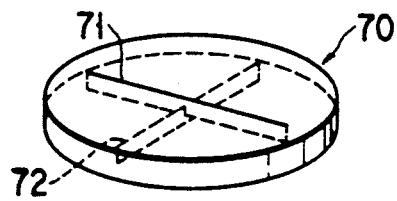
F I G. 6
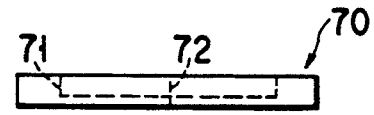
F I G. 7

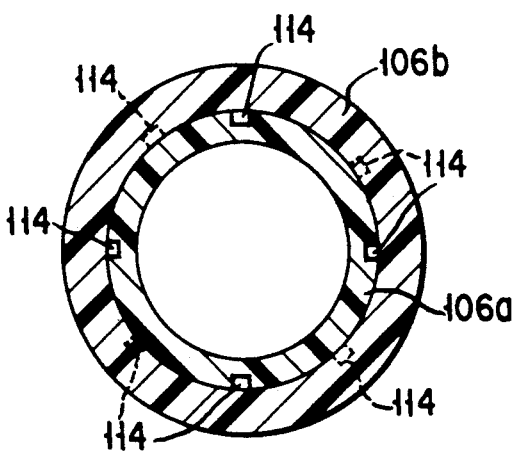
F I G. 12
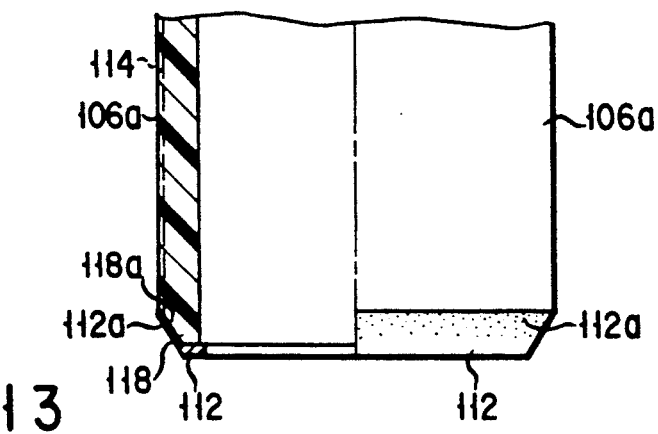
F I G. 13
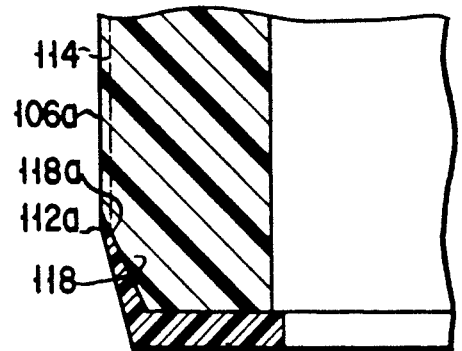
F I G. 14

PIERCING NEEDLE

CROSS-REFERENCES TO THE RELATED APPLICATIONS

This application is a continuation-in-part of U.S. patent application Ser. No. 821,426, filed on Jan. 15, 1992, now U.S. Pat. No. 5,242,411.

BACKGROUND OF THE INVENTION

1. Field of the Invention

The present invention relates to a piercing needle which is temporarily indwelled in a blood vessel in performing, e.g., blood transfusion or fluid therapy.

2. Description of the Related Art

Conventionally, when blood transfusion or fluid transfusion, for example, is to be performed into a blood vessel, a piercing needle is pierced into a blood vessel with its inner and outer needles assembled together. Thereafter, only the inner needle is pulled out, and a connector of, e.g., a blood transfusion set (or a fluid therapy set) is connected to an outer needle hub, thereby performing the operation of interest. However, during the manipulation of pulling out the inner needle and connecting the connector, blood may leak from the outer needle hub. In order to prevent this blood leakage, piercing needles in each of which a valve disc is provided in an outer needle hub have been conventionally proposed (Unexamined Published Japanese Patent Application Nos. 60-88562 and 63-197463).

In such a conventional puncturing needle incorporating a valve disc, however, when an inner needle is pulled out during a manipulation, air remaining in an outer needle hub cannot be vented due to the sealing properties of the valve disc itself. For this reason, the outer hub cannot be filled with blood, and this makes it impossible to confirm a so-called flashback in the outer needle hub unless a an especially cumbersome manipulation is performed.

To solve the above problems, Unexamined Published Japanese Patent Application No. 63-197463 proposes an injection device in which vent means is provided in the side wall of coupling means corresponding to the outer needle hub to vent air from the coupling means chamber and to prevent leakage of a liquid.

The vent means disclosed in the above proposal, however, adopts a structure in which a cylindrical hole is formed in the side wall of the coupling means and a cylindrical filter is fitted in the hole. Therefore, the manufacture of the puncturing needle is complicated and results in a high cost, and there is another disadvantage that the filter may be removed during the manufacture. In addition, during the blood vessel piercing manipulation, the filter portion may be closed with fingers, thus disenabling the reliable confirmation of a flashback. Furthermore, the vent means disclosed in the above proposal has a saddle for preventing blood from being brought into contact with air through the filter. This saddle is formed outside the coupling means and can slide to cover the film. However, this saddle mechanism also has a complicated structure, and this also results in a cumbersome manufacture or a complicated manipulation. In other words, the presence of the saddle may hinder the reliable and easy manipulation of the injection device.

In addition, since the position of the filter is separated from the position of the valve, air in the hub may remain between the filter and the valve disc.

SUMMARY OF THE INVENTION

The present invention has been made so as to solve the above problems and has as its object to the provision of a piercing needle or cannula in which a flashback can be reliably confirmed with a simple structure, in which substantially no air remains in a hub, and blood is not brought into contact with air through a filter thereby increasing the safety of the piercing needle.

In order to achieve the above object, there is provided a piercing needle comprising a cylindrical outer cannula or needle, an outer needle hub fixed to a proximal end of the outer needle and having an internal cavity which communicates with the outer needle, an inner needle which is adapted to be freely inserted in and removed from the outer needle through the outer needle hub such that when inserted in the outer needle a needle tip of the inner needle projects from a distal end of the outer needle, an inner needle hub which is fixed to a proximal end of the inner needle and which can be fitted in the outer needle hub, and a valve disc which is extended to close the internal cavity of the outer needle hub, and through which a rod-like member can be inserted, wherein side holes are formed in a distal end portion of the outer needle to communicate with a gap between the outer and inner needles and with the internal cavity of the outer needle hub, and the outer needle hub is provided with a vent filter which allows the internal cavity of the outer needle hub to communicate with the outer atmosphere, the vent filter being disposed adjacent to the valve disc.

The valve disc has thin a disk-like portion, and cut portions are formed in this disk-like portion. Upon insertion of the rod-like member or the tubular member into this thin-wall portion, the central portion of the valve disc is turned up forward. This turned portion of the valve disc automatically covers the inner circumferential surface of the vent filter.

The inner needle hub which is fitted in the outer needle hub is pierced into a blood vessel. In this case, since the present invention includes the vent filter provided adjacent to the valve disc in the outer needle hub, air originally present in the outer needle hub is pushed out from this filter portion by the blood pressure of blood flowing from the side hole formed in the outer needle. As a result, air which is present close to the valve disc on the inner circumferential surface of the outer needle hub where air is most likely to remain can be removed and replaced with blood.

By connecting the connector as the rod-like member to the outer needle hub, the central portion of the valve disc having the cuts is turned up forward. As a result, the inner circumferential portion of the ring-like vent filter is covered with this turned portion of the valve disc.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 4 is a sectional view taken along a line IV—IV of FIG. 2;

FIG. 5 is a sectional view taken along a line V—V of FIG. 2;

FIG. 6 is a perspective view showing an example of a valve disc;

FIG. 7 is a side view of FIG. 6;

FIG. 12 is a sectional view taken along line XI—XI of FIG. 11;

FIG. 13 is a partially sectional view showing the proximal portion of the first outer needle hub body of the outer needle hub;

FIG. 14 is a sectional view showing part of FIG. 13 in an enlarged scale; and

DETAILED DESCRIPTION OF THE PREFERRED EMBODIMENTS

Figure 1:
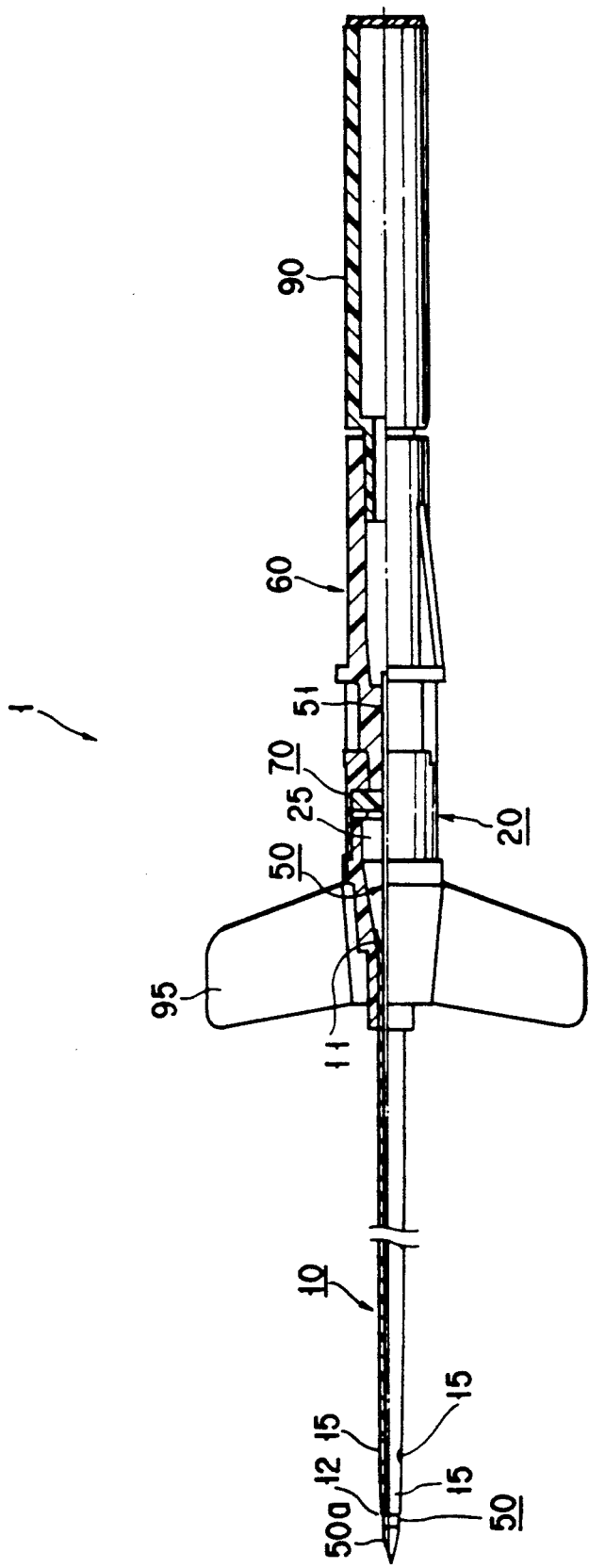
FIG. 1 is a partially sectional view showing a piercing needle according to the present invention.

A first embodiment of a piercing needle according to the present invention will be described below with reference to FIGS. 1 to 10. FIG. 1 is a partially sectional view showing the piercing needle according to the present invention. As shown in FIG. 1, a piercing needle 1 of the present invention has a cylindrical outer needle (cannula) 10; an outer needle hub 20 fixed to a proximal end 11 of the outer needle 10 and having an internal cavity 25 which communicates with the outer needle 10; an inner needle 50 which is provided to be freely inserted in and removed from the outer needle 10 through the outer needle hub 20 and which is fitted in the outer needle 10 so that its needle tip projects from a distal end 12 of the outer needle 10; an inner needle hub 60 which is fixed to a proximal end 51 of the inner needle 50 and can be fitted in the outer needle hub 20; and a valve disc 70 which is extended to close the internal cavity 25 of the outer needle hub 20 and through which a rod-like member or a tubular member (not shown) can be inserted. In addition, the outer needle hub 20 has air vent holes 27 (shown in FIG. 2) which allow the internal cavity 25 of the outer needle hub 20 to communicate with the outer atmosphere. A ring-like vent filter 80 is provided at the end portions of the air vent holes 27 on the internal cavity side.

More specifically, at least one side hole (in this embodiment, three side holes 15 are illustrated) is formed in the distal end portion of the outer cannula or needle 10. Therefore, even when the outer needle 10 and the inner needle 50 are assembled together, the outer atmosphere and the internal cavity 25 of the outer needle hub 20 communicate with each other through these side holes 15. That is, although the distal end 12 of the outer needle 10 is in tight contact with the inner needle 50, a small gap is formed between the outer needle 10 and the inner needle 50 except for that portion. As the outer needle 10, a plastic needle consisting of a fluorine-based resin such as Teflon or an olefine-based resin such as polypropylene or polyethylene is commonly used.

Figure 2:
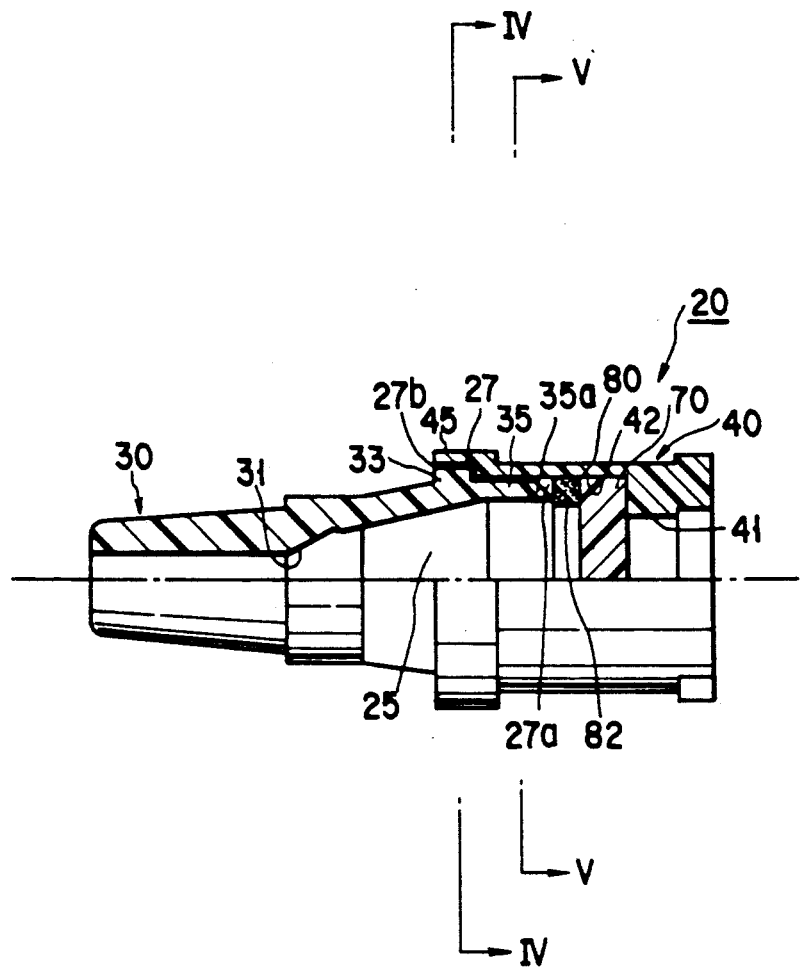
FIG. 2 is a partially sectional view showing an outer needle hub which is one component of the piercing needle according to the present invention.
Figure 3:
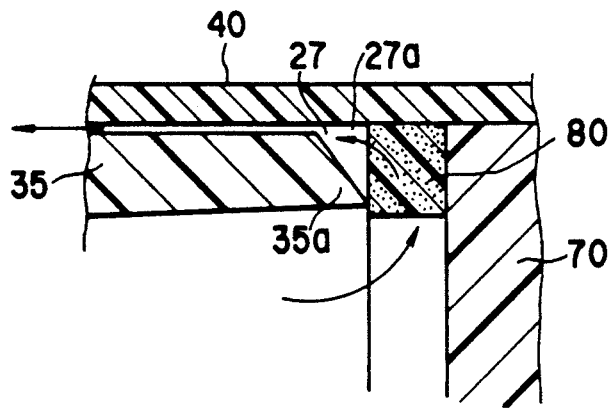
FIG. 3 is an enlarged view showing a portion around a vent filter shown in FIG. 2.

As shown in FIG. 2, the outer needle hub 20 fixed to the proximal end 11 of the outer needle 10 has the air vent holes 27 which allow the internal cavity 25 of the outer needle hub 20 to communicate with the outer atmosphere. In this embodiment, the outer needle hub 20 is constituted by two components, and this facilitates not only the formation of the air vent holes 27 but also the insertion of the vent filter 80 and the valve disc 70 into the outer needle hub 20 as will be described below. That is, the outer needle hub 20 is constituted by two parts, a first outer needle hub body 30 and a second outer needle hub body 40. The first outer needle hub body 30 is substantially cylindrical and has a tapered portion 31 for caulking and fixing the outer needle 10 in its internal cavity. The first outer needle hub body 30 also has a projecting portion 33 and a flat portion 35 on the outer circumferential surface of its rear end portion. A rear end portion 35a of this flat portion 35 is tapered and in contact with the filter 80 to be described later (FIG. 3). In addition, as shown in FIGS. 4 and 5, continuous trenches for forming the air vent holes 27 are formed in the outer circumferential surfaces of the projecting portion 33 and the flat portion 35 of the first outer needle hub body 30. It is preferable to form a plurality of such trenches (air vent holes 27) particularly with equal intervals therebetween along the circumferential direction. The second outer needle hub body 40, on the other hand, is also cylindrical. A tapered surface 41, and more preferably a lure-tapered surface, in which a rod-like member such as a connector (to be described later) is fitted, is formed in the rear portion of an internal cavity of the second outer needle hub body 40. In addition, a recess portion 42 for inserting the valve disc 70 and the vent filter 80 to be described later is formed. The front portion 45 (see FIG. 2) of the second outer needle hub body 40 defines an internal cavity which is shaped such that the projecting portion 33 and the flat portion 35 of the first outer needle hub body 30 are fitted in the portion 45, and this fitting forms the air vent holes 27. As a result, the outer needle hub 20 has a projecting portion on its outer circumferential surface along the circumferential direction, and an outer atmosphere-side end portion 27b of each air vent hole is located on the side surface of this projecting portion. Therefore, even when the piercing needle is handled while the outer circumferential surface of the outer needle hub 20 is held during piercing, these holes are not closed with fingers. Note that in the formation of the air vent holes 27, the trenches need not be formed in the outer circumferential surface of the first outer needle hub body 30 but may be formed in the inner circumferential surface of the second outer needle hub body 40.

The ring-like vent filter 80 is provided at internal cavity-side end portions 27a of the air vent holes 27 in the internal cavity of the outer needle hub 20. This vent filter 80 has pores through which air can pass but a liquid such as blood cannot. The range of the average pore size of the filter 80 may be 0.01 to 0.5 μm, preferably 0.1 to 0.2 μm. The filter is constituted by, e.g., a hydrophobic nonwoven filter consisting of polypropylene or polyethylene, a polypropylene prous film, a sintered hydrophobic filter consisting of a fluorine-based resin or a polyolefin-based resin such as polypropylene or polyethylene, or a swollen filter containing a starch-sodium acrylate graft polymer and polyethylene. The swollen filter is preferably air-permeable before the filter is swollen.

The valve disc 70 is provided behind and adjacent to the vent filter 80. The valve disc 70 especially preferably has a function of preventing a blood leakage from the outer needle hub 20 when the inner needle is pulled out and a connector or the like as the rod-like member is connected during the manipulation, and a function (FIG. 10) in which the central portion of the valve disc is turned up forward (toward the distal end) upon insertion of the rod-like member or the tubular member into the valve disc 70 and this turned portion of the valve disc covers an inner circumferential surface 82 (FIG. 2) of the ring-like vent filter 80. With these functions (particularly the latter), in the situation in which the outer needle 10 is closed while a connector or the like is connected and blood is supplied by a blood pump through the outer needle, a flow of air from the vent filter 80 into the internal cavity 25 can be prevented even if a load is applied on the internal cavity 25, thereby preventing blood from being brought into contact with the outer air through the vent filter 80. A so-called Y-cut valve or cross-cut valve can be used as the valve disc 70 having the above functions. A most preferable practical example is one having a structure similar to that disclosed in Unexamined Published Japanese Patent Application No. 60 88562. That is, as shown in FIGS. 6 and 7. A disk-like portion of this valve, which consists of a flexible substance, such as silicone rubber, is linearly cut from both the upper and lower surfaces, thereby forming first and second cut portions 71 and 72 which cross each other at the substantially central portion.

The assembly of the inner needle hub 60 and the inner needle 50 can be inserted into the assembly of the outer needle hub 20 and the outer needle 10. Note that as shown in FIG. 1, a filter cap 90 having air permeability may be provided in the rear end portion of the inner enable hub 60, or a wing 95 for facilitating fixing may be formed on the lower surface of the outer needle hub 20.

A rotation-stop mechanism (not shown) for adjusting the needle tip of the inner needle 50 is normally provided near the fitted portion of the inner and outer needle hubs 60 and 20.

To visually confirm flashback (i.e., a blood flow into the outer needle hub 20), it is desirable that the first and second outer needle hub bodies 30 and 40 jointly constituting the outer needle hub 20 be formed of a material which has such transparency as enables visual confirmation of a blood flow. Thermoplastic synthetic resins, such as polypropylene, polyethylene, polycarbonate, and polystyrene, can be used for forming the outer needle hub 20 and the inner needle hub 60. It is preferable that such thermoplastic synthetic resins have a certain degree of transparency.

Although the outer needle 10 and the first outer needle hub body 30 can be secured by use of an adhesive or a solvent, it is preferable to avoid the use of such a securing agent. The most desirable securing method is to insert a short metal pipe into the outer needle from the rear end and perform caulking by means of the metal pipe.

Although the outer needle 50 and the inner needle hub 60 can be secured by use of an adhesive or a solvent, it is also preferable to avoid the use of such a securing agent. The most desirable securing method is to form the inner needle hub with a thermoplastic material and perform induction heating thereby fuse-bonding the inner needle hub 60 to the outer needle 50.

The manipulation of the piercing needle described above will be described below.

Figure 8:
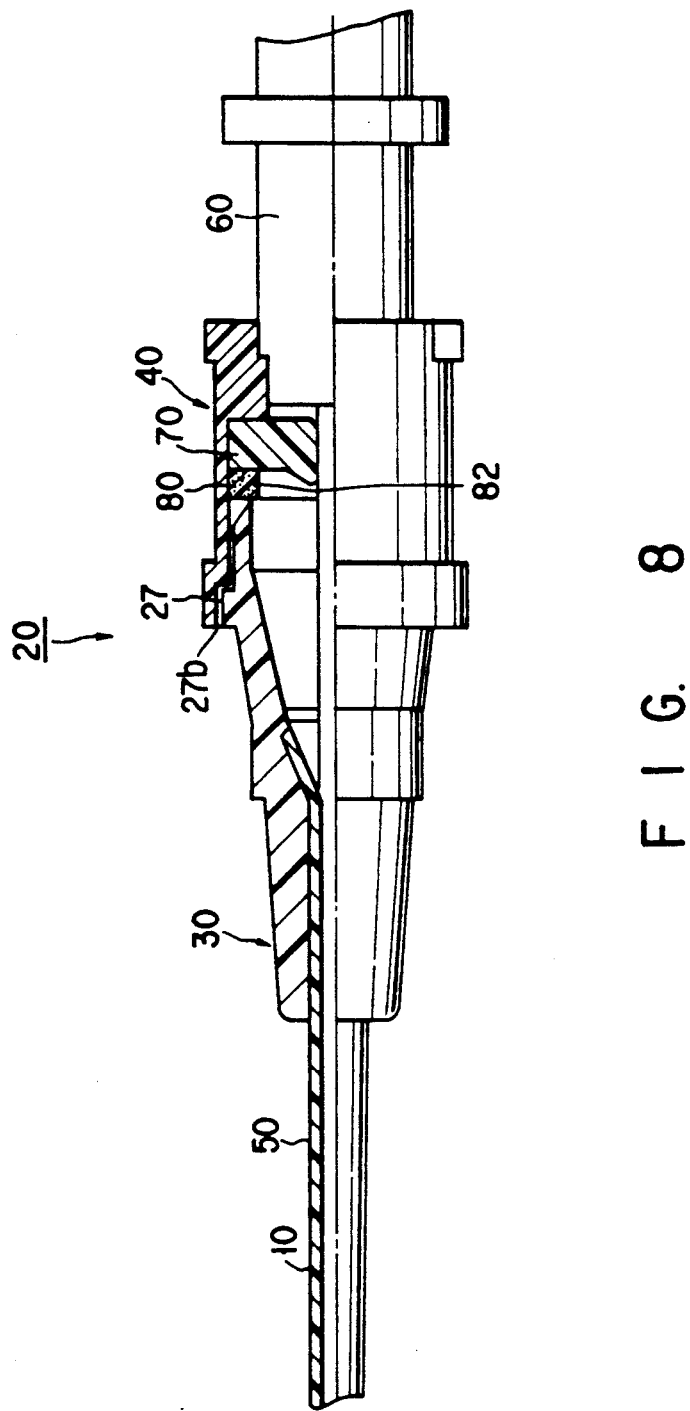
FIG. 8 is a partially sectional view for explaining the manipulation of the piercing needle according to the present invention.
Figure 9:
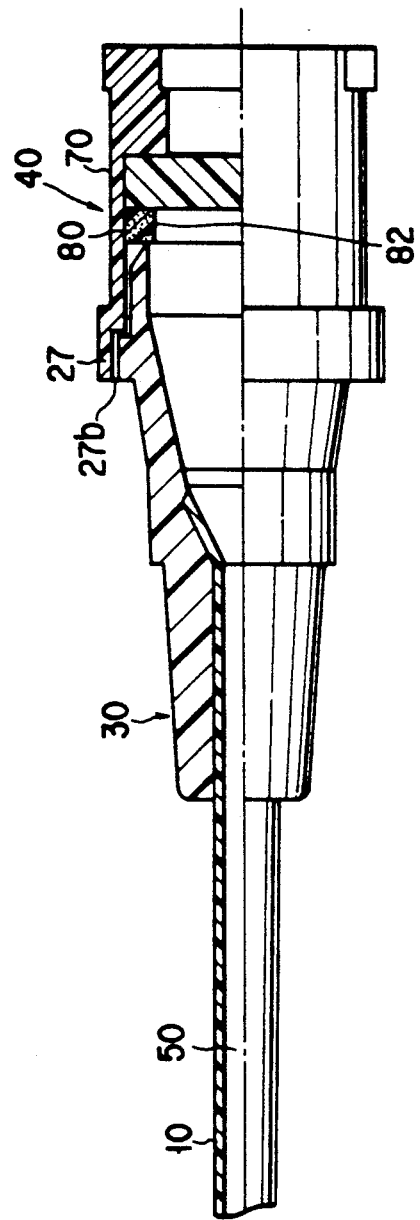
FIG. 9 is a partially sectional view for explaining the manipulation of the piercing needle according to the present invention.

First, as the state before the use, the inner needle 50 is inserted in the outer needle 10 through the outer needle hub 20, as shown in FIG. 1. When the inner needle hub 60 is completely inserted i the proximal end portion of the outer needle hub 20, a needle tip 50a of the inner needle 50 projects from the distal end of the outer needle 10, and this enables smooth piercing into a blood vessel or the like. At this time, the inner needle 50 and the valve disc 70 are in tight contact with each other, as shown in FIG. 8. The piercing needle in this state is pierced into, e.g., a blood vessel to introduce the outer needle 10 and the inner needle 50 together into the blood vessel. In this case, blood flows from the side holes 15 formed in the distal end portion of the outer needle 10 into the internal cavity 25 of the outer needle hub 20. As shown in FIG. 3, air in the outer needle hub 20 is pushed out from the vent filter 80 by a blood pressure and replaced with blood, and this makes it possible to confirm a flashback. Subsequently, the inner needle 50 is pulled out from the outer needle hub 20 (FIG. 9). In this case, the valve disc 70 naturally closes to prevent a blood leakage from the outer needle hub 20. Thereafter, as shown in FIG. 10, a connector 100 as the rod-like member or the tubular member of a blood transfusion or fluid transfusion set (not shown) is inserted in the outer needle hub 20 and fixed such that the distal end portion of the connector 10 extends through the valve disc 70.

Figure 10:
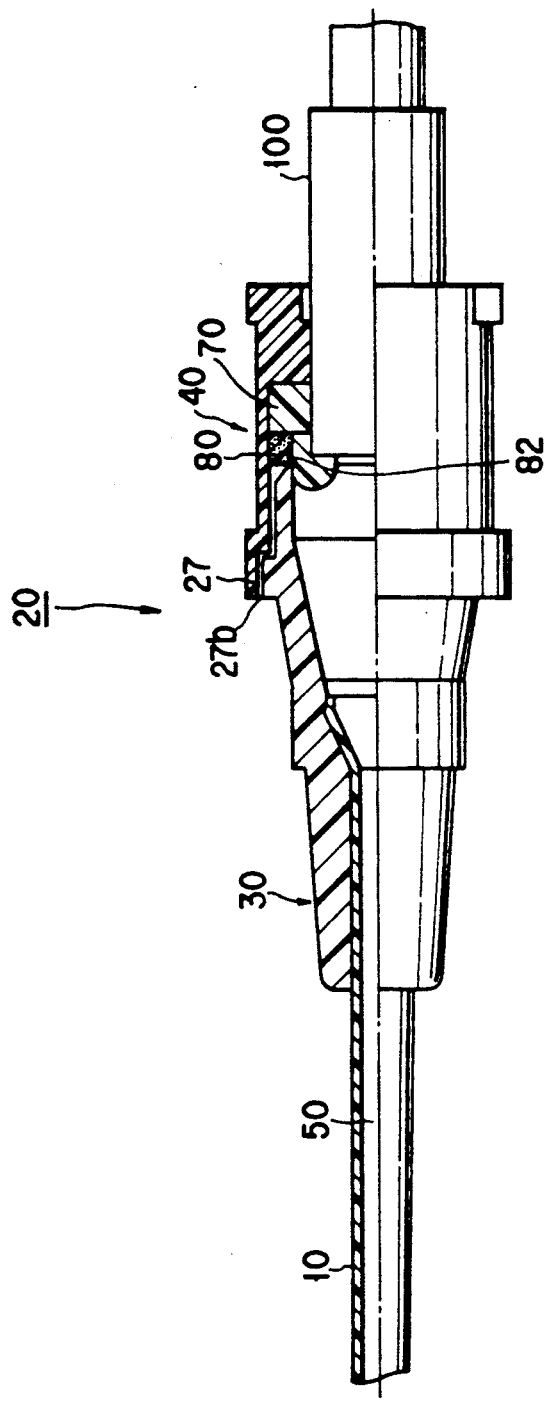
FIG. 10 is a partially sectional view for explaining the manipulation of the piercing needle according to the present invention.

At this time, the valve disc 70 deforms, and this deformation turns up the central portion of the valve disc forward, as shown in FIG. 10. This turned portion of the valve disc consequently covers the inner circumferential surface 82 of the ring-like vent filter.

The outer needle hub of the piercing needle according to the present invention has air vent holes which allow the internal cavity of the outer needle hub to communicate with the outer atmosphere, and the vent filter provided at the internal cavity-side end portions of the air vent holes. Therefore, when the inner needle hub fitted in the outer needle hub is pierced into a blood vessel, air in the outer needle hub is pushed out from this filter portion by a blood pressure and replaced with blood. The result is easy and reliable confirmation of a flashback. The manufacture of this piercing needle is also easy. In addition, since the vent filter is provided adjacent to the valve disc extended in the outer needle hub, it is possible to effectively remove air in a portion close to the valve disc on the inner circumferential surface of the outer needle hub. Furthermore, the outer needle hub has a projecting portion on its outer circumferential surface along the circumferential direction, and the outer atmosphere-side end portions of the air vent holes are formed in the side surface of this projecting portion. Therefore, even when the blood vessel piercing is performed by holding the outer circumferential surface, of the outer needle hub, the air vent holes are prevented from being closed with fingers. When a connector as the rod-like member or the tubular member is connected to the outer needle hub, the central portion of the valve disc having the cuts is turned up forward, and the inner circumferential surface of the ring-like vent filter is covered with this turned portion of the valve disc. As a result, blood is prevented from being brought into contact with the outer air through the vent filter.

In the first embodiment described above, the vent filter 80 is fitted in the recess portion 42 located at the distal end of the second outer needle hub body 40, together with the valve disc 70. However, the vent filter may be coupled to the circumference of the rear end of the first outer needle hub body, as in the second embodiment shown in FIGS. 11 through 14.

The second embodiment will now be described.

As shown in FIGS. 11 through 14, an outer needle hub 106 is constituted by first and second outer needle hub bodies 106a and 106b. A trench-like path 114, which extends from the circumference of the rear end face of the first outer needle hub body 106a, is formed in the outer circumferential surface of the first outer needle body 106a. The trench-like path 114 constitutes a path through which the inside 125 of the outer needle hub 106 and the outside thereof communicate with each other via a ring-like filter 112. Although the trench-like path may be only one in number, two or more trench-like paths are provided in an ordinary case, as shown in FIG. 12. The number of trench-like paths 114 to be provided can be determined arbitrarily. It should be noted that the trench-like path 114 need not be linear. Further, as is indicated by the broken lines in FIG. 12, the trench-like path 114 may be formed in the inner circumferential surface of that portion of the second outer needle hub body 106b which is fitted around the first outer needle hub body 106a. Still further, the trench-like path 114 need not be in the form of a complete "trench". Either a recess or a projection may be provided for the inner circumferential surface of the fitted portion of the second outer needle hub body 106b and/or the outer circumferential surface of the fitted portion of the first outer needle hub body 106a, as long as such a recess or a projection provides a path through which the inside and outside of the outer needle hub 106 communicate with each other. When the first outer needle hub body 106a is fitted into the second outer needle hub body 106b, the trench-like path 114 formed between them permits air to be guided to the outside of the outer needle hub 106, so that the fitting operation can be facilitated.

As shown in FIGS. 13 and 14, the ring-like vent filter 112 is coupled to the rear end of the first outer needle hub body 106a. The ring-like vent filter 112 and the first outer needle hub body 106a are preferably formed of a thermoplastic material so that the ring-like vent filter 112 can be coupled to the first outer needle hub body 106a by thermal melting. The circumference 118 of the rear end portion of the first outer needle hub body 106a has a slanted face, as shown in FIGS. 13 and 14, and the circumference 112a of the ring-like vent filter 112 is adhered to the slanted face of the circumference 118a of the first outer needle hub body 106a. As shown in FIG. 14, the ring-like vent filter 112 is adhered only at the circumference. It should be noted that the circumference 118 of the rear end portion of the first outer needle hub body 106a is not limited to the slanted face; it may be a curved face instead. (In the specification of this application, the concept of "being slanted" is intended to cover a curved face.) In short, the circumference of the rear end portion of the first outer needle hub body 106a is chamfered such that it is either tapered or curved.

As mentioned above, the circumference 118 of the rear end portion of the first outer needle hub body 106a is slanted, and only the circumference of the ring-like vent filter 112 is adhered thereto. With this structure, the ring-like vent filter 112 forms an air passage, except for its adhered portion. Since the air passage of the vent filter 112 is not blocked by the adhered portion, air can be reliably discharged from the inside of the outer needle hub 106. In general, in medical devices, the use of an adhesive or a solvent should be avoided since the adhesive or solvent, if used, may elute during use. For this reason, the second embodiment does not use any adhesive for coupling the ring-like vent filter 112 and the outer needle hub 106 together. As mentioned above, the vent filter 112 and the outer needle hub 106 are preferably formed of a thermoplastic material, and the former is adhered to the latter by thermal melting. If the vent filter 112 is adhered to the outer needle hub 106 merely by thermal melting, the meshes of the vent filter 112 may be thermally destroyed at the melted portion, blocking the air passage of the filter. This is why only the circumference of the vent filter 112 is adhered to the slanted circumference 118 of the rear end portion of the first outer needle hub body 106a.

A filter of any type can be employed as the ring-like vent filter 112, as long as it permits transmission of a gas and prevents flow of a liquid such as blood. The vent filter 112 should be as thin as possible. To be specific, it is preferable that the vent filter 112 be made by an unwoven fabric formed of a thermoplastic material, such as polypropylene, polyethylene, nylon, or polyester. In the second embodiment, a polypropylene unwoven fabric (weight: 120 g/m$^2$: TONEN TAPYRUS, P120UA04 is adopted as the vent filter 112. The width of the vent filter 112 is not limited to a specific value, but is preferably somewhat larger than the thickness of the first outer needle hub body 106 (1.6 times or so). The inner diameter of the vent filter 112 can be determined in accordance with the diameter of the first outer needle hub body 106a, but the inner diameter of the smallest portion of the vent filter 106 is normally selected within the range of 4.5 to 5.0 mm. The thickness of the vent filter 112 is preferably within the range of 0.1 to 0.5 mm, and the width of the melted portion (coupled portion) of the vent filter is preferably within the range of 0.1 to 0.5 mm.

The second outer needle hub body 106b has a cylindrical shape, and its rear end is tapered such that a rod-like member (e.g., a connector) can be engaged therewith. The second outer needle hub body 106b has an annular groove 136 formed in the inside thereof, and the annular portion 110a of an elastic valve disc 110 is fitted into the annular groove 136. The distal end portion of the second outer needle hub body 106b has such a shape as enables insertion therein of the proximal end portion 133 of the first outer needle hub body 106a. The trench-like paths 114 mentioned above are defined between the distal end portion of the second outer needle hub body 106b and the proximal end portion 133 of the first outer needle hub body 106a, such that the trench-like paths 114 are spaced at equal intervals in the circumferential direction. Since the trench-like paths 114 are arranged uniformly in the circumferential direction of the coupled portion between the first and second outer needle hub bodies 106a and 106b, they are not completely blocked by the fingers of the operator at the time of a piercing operation. In addition, since the trench-like paths are not exposed to the outer circumferential surface of the outer needle hub 106 it is not likely that the trench-like paths will be easily clogged.

Figure 11:
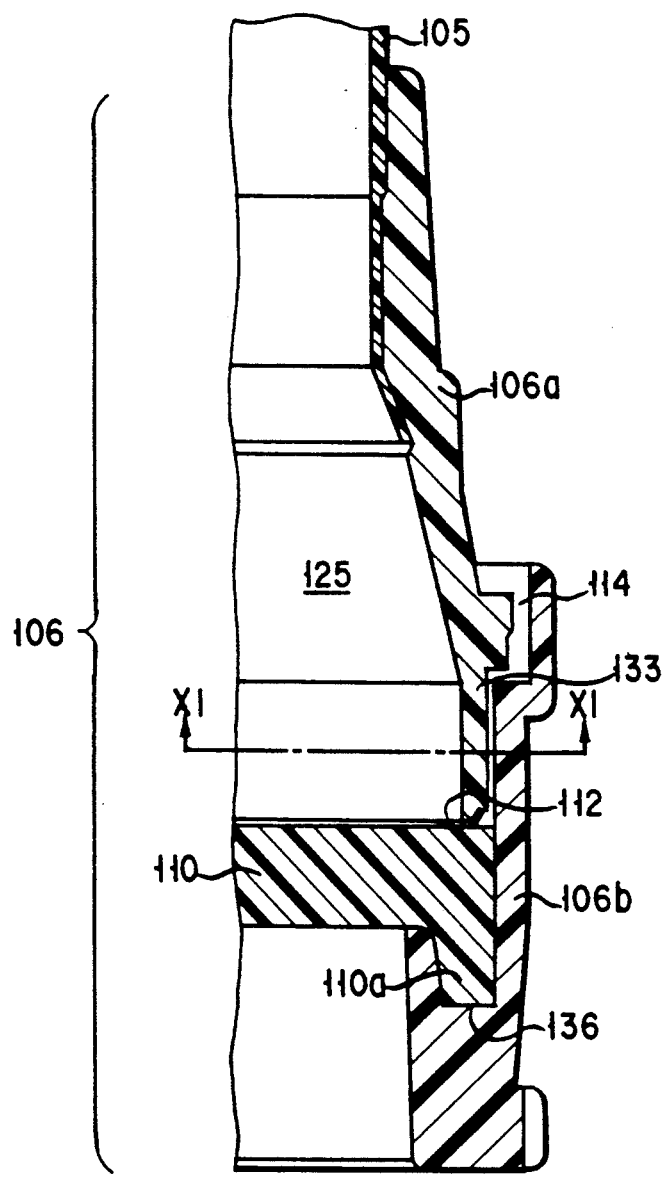
FIG. 11 is a partially sectional view showing an outer needle hub according to the second embodiment of the present invention.
Figure 15:
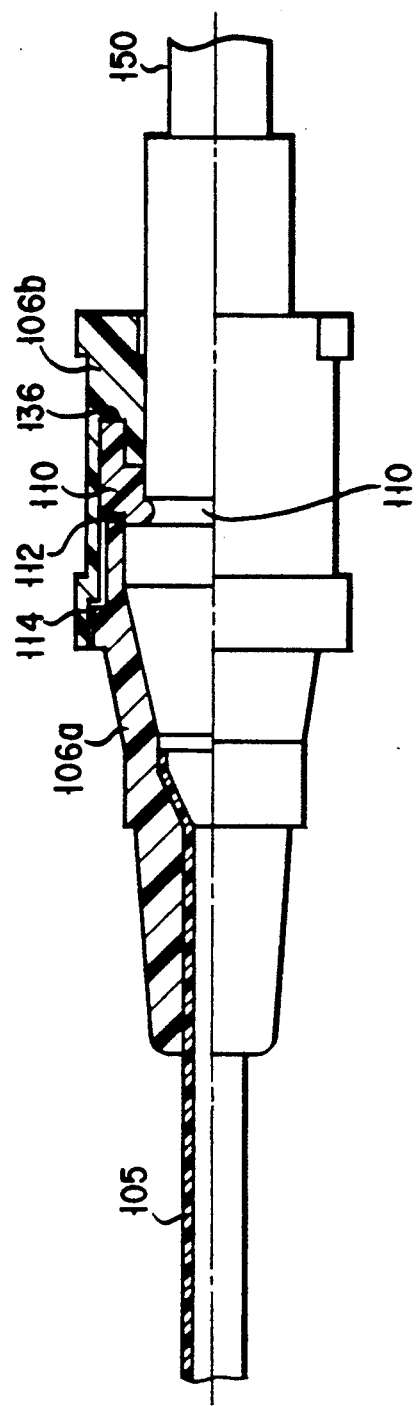
FIG. 15 is a partially sectional view illustrating how to use the piercing needle shown in FIG. 11.

As shown in FIG. 11, the elastic disc 110 occupies part of the internal space of the second outer needle hub 106b so as to block the passageway thereof. The ring-like vent filter 112 is clamped between the valve disc 110 and the first outer needle hub body 106 in such a manner that no air gap is provided between the valve disc 110 and the ring-like vent filter 112 and between the ring-like vent filter 112 and the rear end face (a non-fuse-bonded portion) of the first outer needle hub body 106a. With this structure, the inflow of blood is prevented.

The elastic valve disc 110 has an annular portion 110a, and this annular portion 110a is fitted into the annular groove 136 of the second outer needle hub body 106b. The elastic valve disc 110 of the second embodiment is similar in structure to that of the first embodiment. The elastic valve disk 110 has an insertion portion, into which either an inner needle (not shown) or the end portion of the connector of a blood (or liquid) transfusion set can be inserted in a liquid tight manner. When the inner needle or the connector of a blood transfusion set, a liquid transfusion set or a dialyzing circuit is not inserted, the insertion portion of the elastic valve disc 110 is kept in the closed state where a blood flow is prevented. When the inner needle is inserted, the insertion portion of the elastic valve disk 110 does not close the ring-like vent filter 112. When the connector or a rod-like member 150 having a larger outer diameter than that of the inner needle is inserted, the central portion of the elastic valve disc 110 is turned up and swells toward the ring-like vent filter 112. The swelled portion of the elastic valve disc 110 covers the ring-like vent filter 112, and the tip end of the swelling portion is pressed against the inner surface of the first outer needle hub body 106a. As a result, the ring-like vent filter 112 is entirely covered.

Because of the above-mentioned function of the elastic valve disc 110, a liquid (blood or liquefied medicament) flowing into the outer needle hub 106 is prevented from being exposed to the atmosphere through the ring-like vent filter 112. When a connector or the like is coupled and blood is drawn through the outer needle 105 by means of a blood pump, it may happen that the outer needle will be clogged, producing a negative pressure in the inside 125 of the outer needle hub 106. Even in this situation, the trench-like paths 114 and the ring-like vent filter 112 prevent air from flowing into the inside 125 of the outer needle hub 106. Accordingly, air does not flow into a circuit (e.g., a dialyzing circuit) connected to the outer needle hub 106.

Since the needle of the second embodiment is used in the same way that of the first embodiment, a description of how to use it will be omitted herein.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A piercing needle comprising:
   a cylindrical outer needle;
   an outer needle hub fixed to a proximal end of said outer needle, said outer needle hub having an internal cavity which communicates with said outer needle;
   an inner needle freely insertable into and removable from said outer needle through said outer needle hub such that when said inner needle is inserted in the outer needle a needle tip of said inner needle projects from a distal end of said outer needle and a gap is formed between said outer and inner needles; and
   an inner needle hub fixed to a proximal end of said inner needle, said inner needle hub fitting in said outer needle hub;
   said outer needle hub comprising:
   a cylindrical first outer needle hub body coupled to a proximal end of said outer needle;
   a cylindrical second outer needle hub body fixed to a rear end of said first outer needle hub body;
   an elastic valve disc located between said first and second outer needle hub bodies and permitting a rod member to be inserted thereto, said elastic valve disc sealing said internal cavity of said outer needle hub;
   a ring shaped vent filter located between said elastic valve disc and said first outer needle hub body; and
   a communication path means for communicating the inside of said outer needle hub with the outside thereof by means of said ring shaped vent filter.

2. A piercing needle according to claim 1, wherein:
   said rear end of said first outer needle hub body has a slanted circumferential face; and
   said ring shaped vent filter has a circumferential portion coupled to said slanted circumferential face of said rear end of said first outer needle hub body.

3. A piercing needle according to claim 1, wherein said first and second outer needle hub bodies are secured to each other by fitting said rear end of said first outer needle hub body into a distal end of said second outer needle hub body.

4. A piercing needle according to claim 1, wherein said communication path means includes at least one trench formed in an outer surface of said first outer needle hub body, said trench extending from the circumference of said rear end of said first outer needle hub body toward a distal end of said first outer needle hub body.

5. A piercing needle according to claim 1, wherein said communication path means includes at leas one trench formed in an inner surface of said second outer needle hub body, said trench being located in a region where said second outer needle hub body is fitted around said first outer needle hub body.

* * * * *